(12) United States Patent
Sullivan et al.

(10) Patent No.: US 10,603,398 B2
(45) Date of Patent: Mar. 31, 2020

(54) PORTABLE DIFFUSER AND RELATED METHODS

(71) Applicant: Scentsy, Inc., Meridian, ID (US)

(72) Inventors: Mark Sullivan, Meridian, ID (US);
Travis Dean, Meridian, ID (US);
Joseph B. Mason, Nampa, ID (US);
Martin Stenger, Boise, ID (US);
Mariel Schweitzer, Boise, ID (US); R. Orville Thompson, Eagle, ID (US)

(73) Assignee: Scentsy, Inc., Meridian, ID (US)

( * ) Notice: Subject to any disclaimer, the term of this patent is extended or adjusted under 35 U.S.C. 154(b) by 81 days.

(21) Appl. No.: 15/650,221

(22) Filed: Jul. 14, 2017

(65) Prior Publication Data

US 2019/0015539 A1    Jan. 17, 2019

(51) Int. Cl.
*A61L 9/03* (2006.01)
*A61L 9/12* (2006.01)

(52) U.S. Cl.
CPC .............. *A61L 9/032* (2013.01); *A61L 9/122* (2013.01); *A61L 2209/12* (2013.01); *A61L 2209/132* (2013.01); *A61L 2209/133* (2013.01)

(58) Field of Classification Search
CPC ................................. A61L 9/032; A61L 9/122
See application file for complete search history.

(56) References Cited

U.S. PATENT DOCUMENTS

| 5,935,526 A * | 8/1999 | Moore ................... A61L 9/122 239/56 |
| 6,511,531 B1 * | 1/2003 | Cartellone ............... A61L 9/03 261/142 |
| 6,631,888 B1 | 10/2003 | Prueter |
| 7,824,627 B2 * | 11/2010 | Michaels .............. A01M 1/205 239/102.2 |
| 7,887,760 B2 * | 2/2011 | Yamamoto .......... A01M 1/2033 422/124 |
| 8,783,888 B2 * | 7/2014 | McCavit ................. A61L 9/122 362/96 |
| 2009/0109663 A1 | 4/2009 | Tsai |
| 2010/0090022 A1 * | 4/2010 | Hayashida .............. A61L 9/122 239/99 |

(Continued)

OTHER PUBLICATIONS

European Extended Search Report for European Application No. 18177415.9, dated Jan. 7, 2019, 11 pages.

*Primary Examiner* — Regina M Yoo
(74) *Attorney, Agent, or Firm* — TraskBritt

(57) ABSTRACT

A diffuser includes a base, a fan mounted to the base, a receptacle provided over the fan and mounted to the base, a sleeve mounted on the upper surface of the base and enclosing the fan and receptacle, and a lid mounted over the sleeve. Each of the base and the lid comprises at least one opening formed about a periphery thereof. The receptacle comprises a bottom wall with a plurality of opening formed therethrough and a vertically extending sidewall to retain a fragrant medium therein. The fan forces airflow from an exterior of the diffuser, into the base through the at least one opening, through the plurality of openings formed in the bottom wall of the receptacle, through the receptacle and about any fragrant medium therein, into a volume of space above the receptacle enclosed by the lid, and out through the at least one opening in the lid.

19 Claims, 8 Drawing Sheets

(56) References Cited

U.S. PATENT DOCUMENTS

2010/0284168 A1* 11/2010 Walter ................. A01M 1/205
362/96
2013/0136432 A1    5/2013 Cheung
2015/0297774 A1   10/2015 Thompson et al.
2016/0318059 A1   11/2016 Osborn et al.

* cited by examiner

PORTABLE DIFFUSER AND RELATED METHODS

TECHNICAL FIELD

Embodiments of the present disclosure relate generally to diffusers for diffusing fragrance into the ambient air, and to methods of assembling and using such diffusers.

BACKGROUND

Diffusers are devices that are used to generate atomized droplets of a liquid and to disperse the atomized droplets of liquid into the ambient air surrounding the diffuser. For example, some diffusers are used for humidification. Diffusers are also used for aroma therapy, wherein scented oils or other therapeutic liquids are atomized and dispensed into the surrounding ambient air. Diffusers often employ an ultrasonic transducer to generate ultrasonic vibrations in a bath of liquid held within the diffuser. A fan is used to generate airflow through the diffuser, the airflow carrying the atomized droplets of liquid generated by the ultrasonic transducer out from the diffuser and into the surrounding ambient air.

BRIEF SUMMARY

In some embodiments, the present disclosure includes a diffuser for diffusing a fragrant air into surrounding ambient air includes a base, a fan mounted to the base over an upper surface thereof, a receptacle provided over the fan and mounted to the base over the upper surface thereof, a sleeve mounted on the upper surface of the base and enclosing the fan and the receptacle, and a lid mounted over the sleeve. The base comprises at least one opening formed about a periphery of the base and extending between a lower surface and an upper surface of the base. The receptacle comprises a bottom wall and a vertically extending sidewall to retain a fragrant medium therein. The bottom wall of the receptacle comprises a plurality of openings formed therethrough. The lid comprises at least one opening formed about a periphery of the lid and extending between a lower surface and an upper surface of the lid. The fan is configured to force airflow from an exterior of the diffuser, into the base through the at least one opening of the base, through the plurality of openings formed in the bottom wall of the receptacle, through the receptacle and about any fragrant medium therein, into a volume of space above the receptacle and enclosed by the lid, and out through the at least one opening in the lid to the ambient air external to the diffuser.

In other embodiments, the present disclosure includes a method of assembling a diffuser for diffusing fragrant air into surrounding ambient air. The method includes providing a diffuser comprising a base comprising at least one opening, a fan mounted to the base over the upper surface thereof, a receptacle provided over the fan and mounted to the base over the upper surface thereof, and a sleeve mounted on the upper surface of the base and enclosing the fan and the receptacle. The at least one opening of the base is formed about a periphery of the base and extends between a lower surface and an upper surface of the base. The receptacle comprises a bottom wall and a vertically extending sidewall. The bottom wall of the receptacle comprises a plurality of openings formed therethrough. The method further includes disposing an at least partially solid fragrant medium in the receptacle and coupling a lid to the sleeve. The lid comprises at least one opening formed about a periphery of the lid and extending between a lower surface and an upper surface of the lid.

In yet other embodiments, the present disclosure includes a method of using a diffuser for diffusing a fragrance into surrounding ambient air. The method includes providing a diffuser comprising a base comprising at least one opening, a fan mounted to the base over an upper surface thereof, a receptacle provided over the fan and mounted to the base over an upper surface thereof, and a sleeve mounted on the upper surface of the base and enclosing the fan and the receptacle. The at least one opening of the base is formed about a periphery of the base and extends between a lower surface and an upper surface of the base. The receptacle comprises a bottom wall and a vertically extending sidewall. The bottom wall comprises a plurality of openings formed therethrough. The method further includes disposing an at least partially solid fragrant medium within the receptacle. The at least partially solid fragrant medium emits a fragrance. A lid is provided on the sleeve and has at least one opening formed about a periphery thereof. The at least one opening extends between a lower surface and an upper surface of the lid. The method further includes supplying power to the fan such that airflow is forced from an exterior of the diffuser, into the base through the at least one opening of the base, through the plurality of openings formed in the bottom wall of the receptacle, through the receptacle and about the at least partially solid fragrant medium therein, into a volume of space above the receptacle and enclosed by the lid, and out through the at least one opening in the lid to ambient air external to the diffuser and such that the fragrance emitted by the at least partially solid fragrant medium is carried by the airflow to the ambient air external to the diffuser.

DETAILED DESCRIPTION

Figure 1:
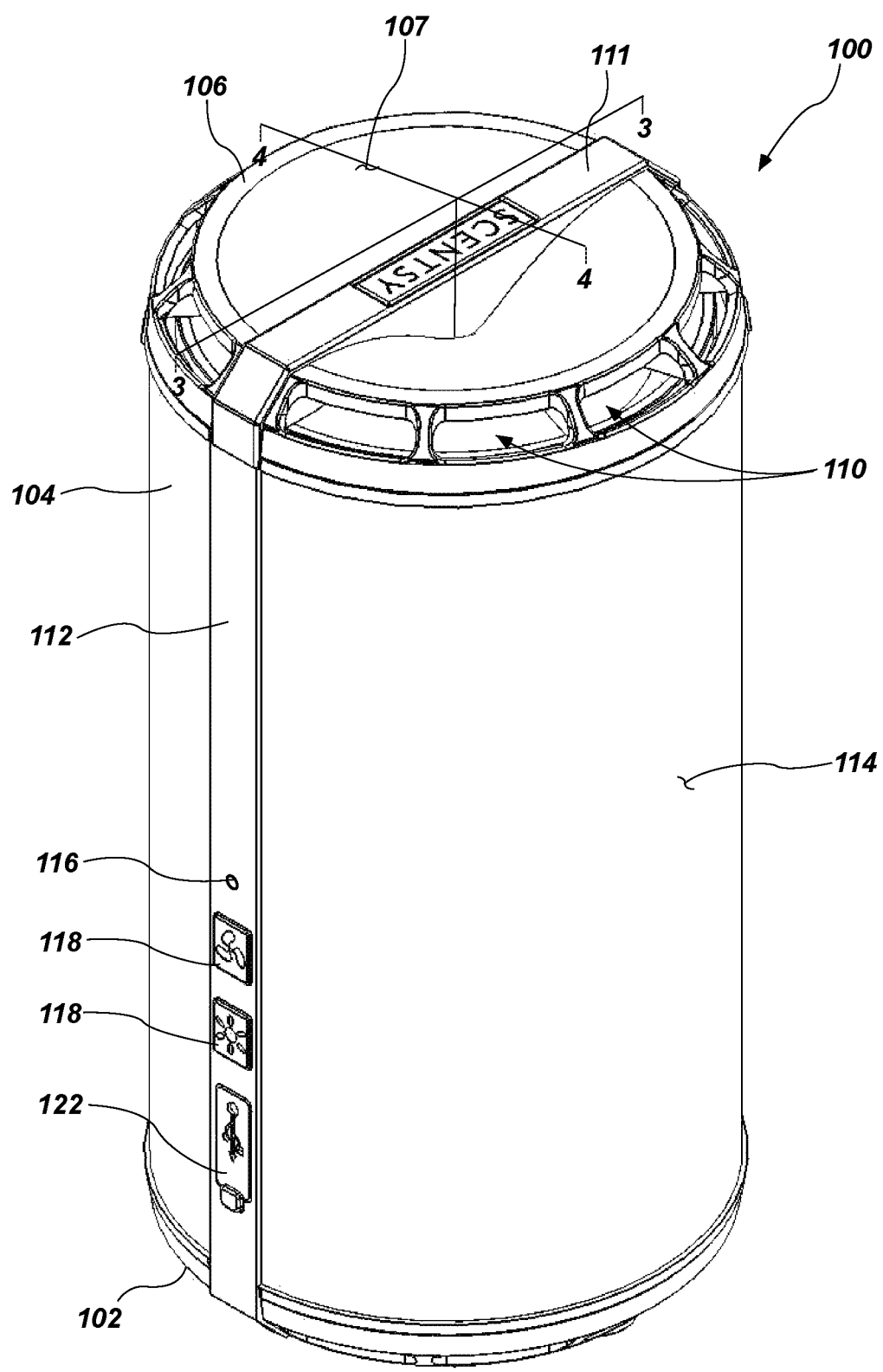
FIG. 1 is a perspective view of a diffuser for diffusing fragrant air into surrounding ambient air according to an embodiment of the present disclosure.

The illustrations presented herein are not meant to be actual views of any particular diffuser, component thereof, or method, but are merely idealized representations that are employed to describe certain embodiments of the present disclosure. For clarity in description, various features and elements common among the illustrated embodiments may be referenced with the same or similar reference numerals.

As used herein, any directional term (e.g., upper, lower, side, top, bottom, etc.) refers to a direction relative to the diffuser when the diffuser is used during normal operation. By way of non-limiting example, a vertical portion of a diffuser is the vertical portion while the diffuser is placed on a surface in an orientation for use, and used to diffuse fragrance into the ambient air.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "and/or" includes any and all combinations of one or more of the associated listed items.

Figure 2:
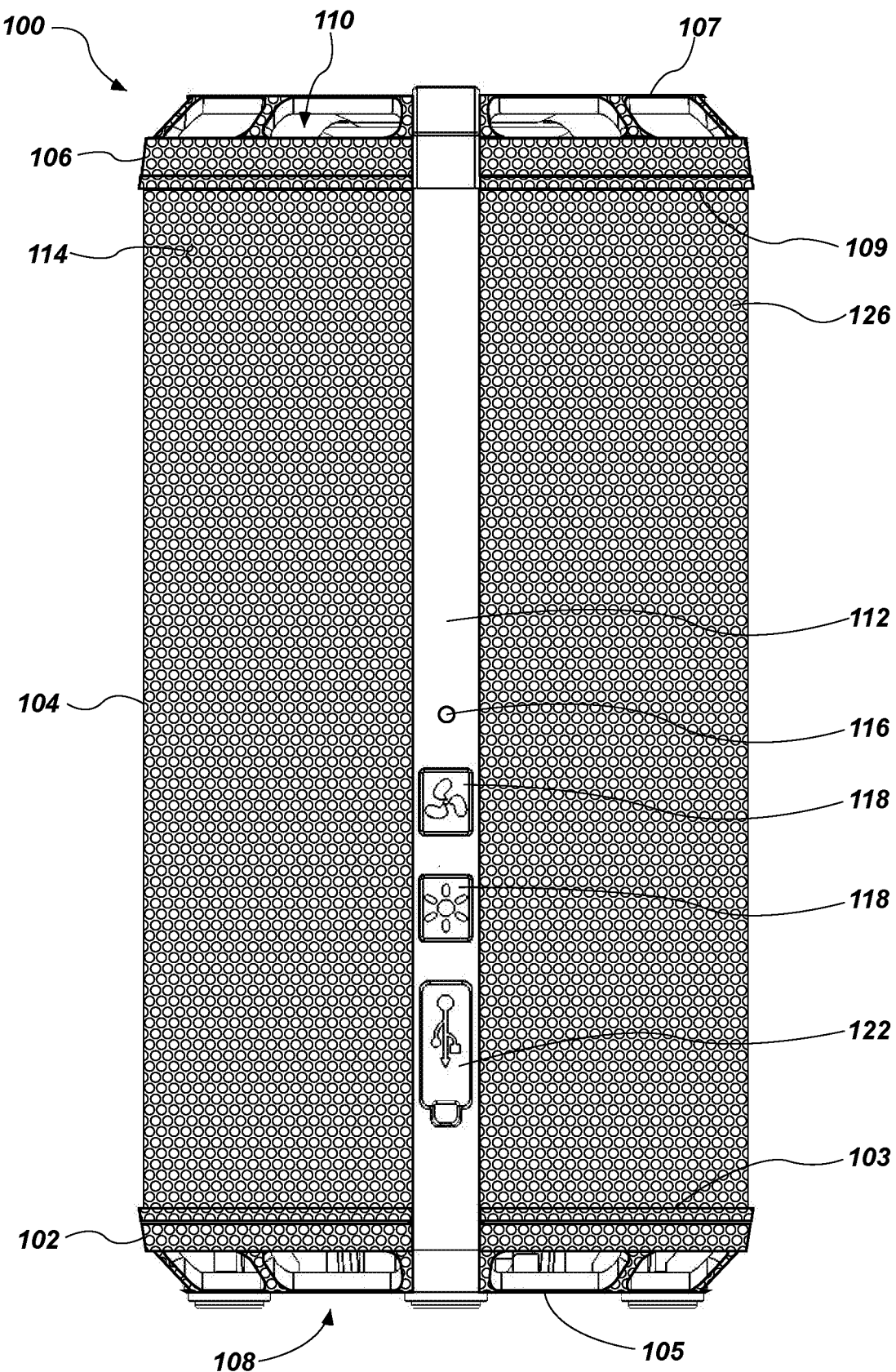
FIG. 2 is a side view of the diffuser of FIG. 1.

FIGS. 1 and 2 illustrate a perspective view and a side view, respectively, of a diffuser 100 for diffusing fragrance into surrounding ambient air according to embodiments of the present disclosure. The diffuser 100 may comprise a base 102, a sleeve 104, and a lid 106. The base 102 may comprise one or more openings 108 through which airflow may be drawn into the diffuser 100. The openings 108 may be spaced about a perimeter (e.g., circumference) of the base 102 and may extend between an upper surface 103 and a lower surface 105 of the base 102. The sleeve 104 may rest upon the upper surface 103 of the base 102. In some embodiments, the sleeve 104 may comprise a hollow cylinder having a vertically extending sidewall 114. The lid 106 may be coupled to the sleeve 104 on an upper end of the sidewall 114 opposite which the sleeve 104 abuts against the base 102. The lid 106 may comprise one or more openings 110 through which forced airflow may be removed from the diffuser 100. The openings 110 may be spaced about a perimeter of the lid 106 and may extend between an upper surface 107 and a lower surface 109 of the lid 106. The lid 106 may further comprise a handle 111 extending across at least a portion of the diameter thereof.

The diffuser 100 may further comprise at least one plate 112 extending vertically along the sidewall 114 of the sleeve 104. The plate 112 visible in FIGS. 1 and 2 comprises one or more openings 116 formed therethrough for a light, one or more pushbuttons 118, and a Universal Serial Bus (USB) connector 120 (FIG. 3) having a cover 122 thereover. The cover 122 may be hinged to the plate 112 such that the cover 122 may be removed while a battery 150 (FIG. 3) is charged and may cover the USB connector 120 while the battery 150 is not being charged. The cover 122 may be formed of silicone. A second plate 124 (FIG. 3) may extend vertically along the sidewall 114 of the sleeve 104 on a side of the sleeve 104 opposite the first plate 112. In some embodiments, the second plate 124 may lack any openings formed therethrough.

In some embodiments, an exterior surface of at least one of the base 102, the sleeve 104, and the lid 106 may be textured. In other words, the exterior surface of at least one of the base 102, the sleeve 104, and the lid 106 may comprise a plurality of raised and/or recessed structures 126 arranged in a pattern. In other embodiments, the exterior surface of at least one of the base 102, the sleeve 104, and the lid 106 may lack any such structures 126 such that the exterior surface is untextured (e.g., smooth).

Figure 3:
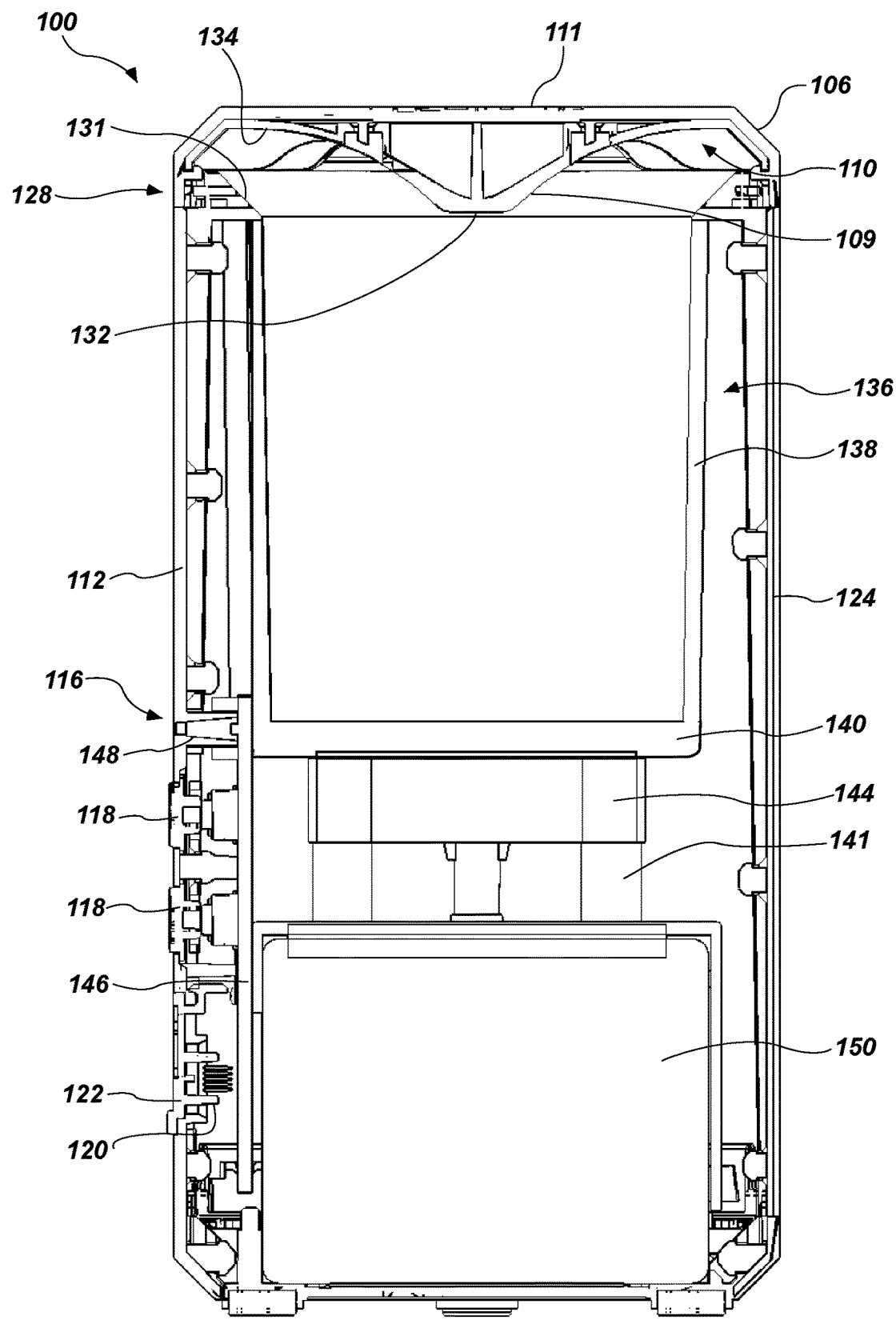
FIG. 3 is a cross-sectional view of the diffuser of FIG. 1, cut-away along plane 3-3 in FIG. 1.
Figure 4:
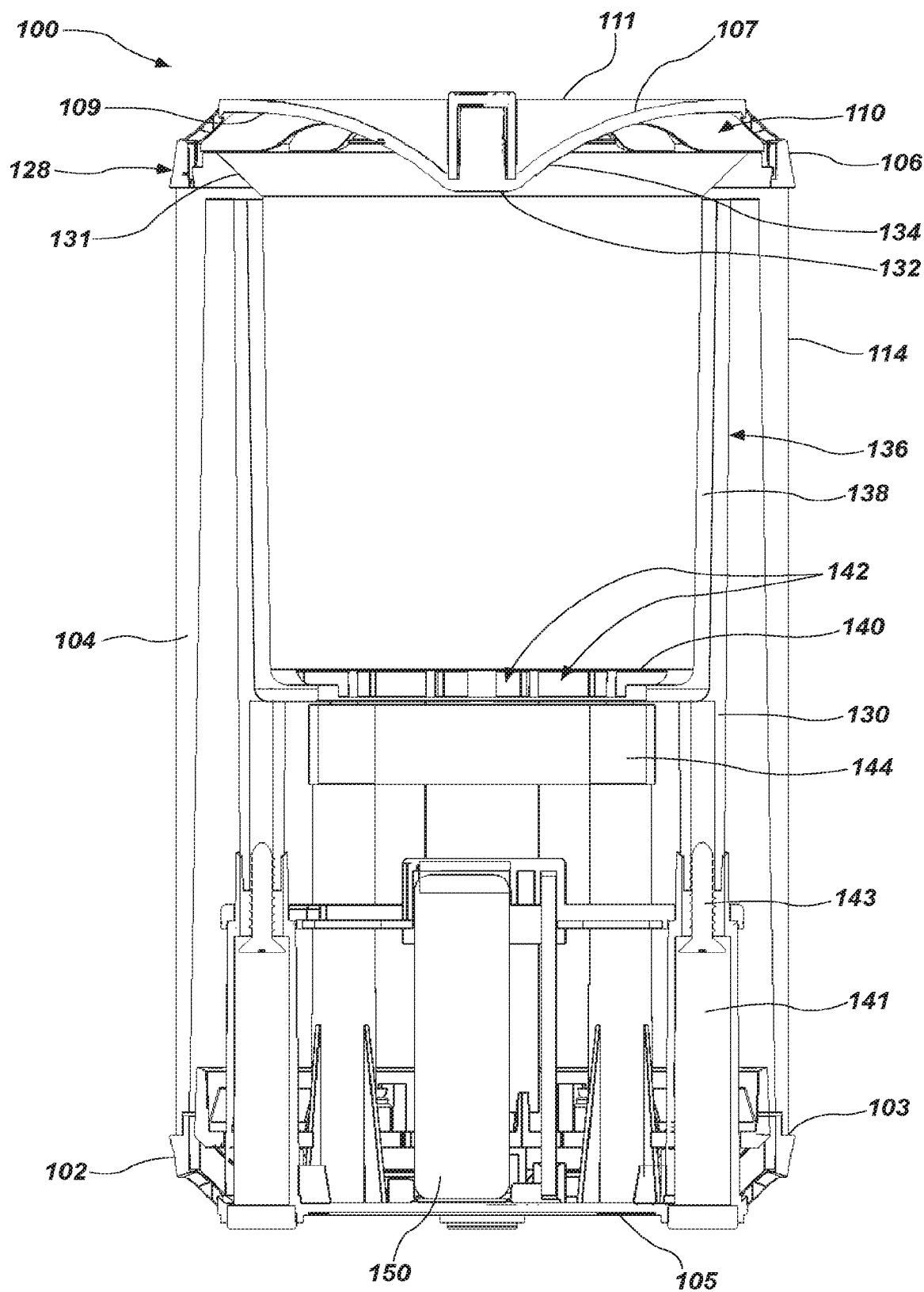
FIG. 4 is a cross-sectional view of the diffuser of FIG. 1, cut-away along plane 4-4 in FIG. 1.

FIGS. 3 and 4 illustrate cross-sectional side views of the diffuser 100. The side views of FIGS. 3 and 4 are taken in a plane that extends parallel to and includes a longitudinal axis of the diffuser 100 along plane 3-3 and 4-4, respectively, of FIG. 1. In some embodiments, the lid 106 may be removably coupled to the sleeve 104. By way of example and not limitation, each of the sleeve 104 and the lid 106 may comprise threading 128 such that the lid 106 may be retained on the sleeve 104. The lid 106 and/or the sleeve 104 may be rotated to engage or disengage the threading 128 such that the lid 106 may be coupled to or separated from the sleeve 104. For example, a user may grip the handle 111 provided on the upper surface 107 of the lid 106 to rotate the lid 106 between an engaged and disengaged position.

With continued reference to FIGS. 3 and 4, the lower surface 109 of the lid 106 may define an upper end of an interior of the diffuser 100. In some embodiments, the lower surface 109 may have a curved, cone shape. By way of example and not limitation, the lower surface 109 may have a generally frustoconical shape defined by a generally planar, central surface 132 and a curved surface 134 extending circumferentially about the central surface 132 and toward the openings 110 in the lid 106 to form a sidewall of the frustoconical shape. In operation, airflow, which may carry a fragrance, may impinge against the central surface 132 and be forced along the curved surface 134 and toward the openings 110 in the lid 106 to diffuse airflow out of the diffuser 100. As best illustrated in FIG. 1, the upper surface 107 of the lid 106 may have a shape similar to that of the lower surface 109. For example, the shape of the upper surface 107 may be reciprocal to the shape of the lower surface 109.

The diffuser 100 may comprise a receptacle 136 having surfaces for retaining a fragrant medium therein. The receptacle 136 may comprise a generally cylindrical sidewall 138 extending substantially vertically toward a substantially planar bottom wall 140. The inner surface of the sidewall 138 and the upper surface of the bottom wall 140 may define the receptacle 136 for retaining the fragrant medium. In some embodiments, the sleeve 104 may be adjoined with or integrally formed with the cylindrical sidewall 138. For instance, the receptacle 136 may further comprise a rim 131 that extends vertically upward and radially outward from the sidewall 138 toward the sidewall 114. As best illustrated in FIG. 4, the bottom wall 140 may comprise one or more openings 142 formed therethrough such that airflow may pass into and through the receptacle 136. In some embodiments, the openings 142 may be concentrically arranged about a longitudinal axis of the diffuser 100.

The receptacle 136 may be mounted over the upper surface 103 of the base. 102. As shown in FIG. 4, the receptacle 136 may be indirectly mounted to the base 102 by way of one or more support columns 130. The support columns 130 may be adjoined with or integrally formed with the bottom wall 140 of the receptacle 136. The support columns 130 may be mounted on one of more support columns 141 extending from the upper surface 103 of the base 102. In some embodiments, the support columns 130 may be coupled to the support columns 141 by screws 143.

The diffuser 100 may further comprise a fan 144. The fan 144 may be provided vertically below the bottom wall 140 of the receptacle 136 and vertically above the upper surface 103 of the base 102. In some embodiments, at least a portion of the fan 144 may abut against the bottom wall 140. The fan 144 may be indirectly mounted to the base 102 by the support columns 141. In operation, the fan 144 is configured to force airflow carrying a fragrance from a fragrant medium retained in the receptacle 136 to the ambient air exterior to the diffuser 100 through the openings 110 of the lid 106. More particularly, the fan 144 forces airflow from an exterior of the diffuser 100, into the base 102, into the receptacle 136, through a fragrance medium (not shown) held within the receptacle 136, through a volume of space between the receptacle 136 and the lid 106, and out through the openings 110 to the ambient air external to the diffuser 100.

The fan 144 may operate at one or more speeds. In one operational mode, the fan 144 may rotate at a single, continuous speed. In another operational mode, the fan 144 may cycle between rotating at a relatively high speed and a relatively low speed for a duration of time, such as a few seconds or more, or a few minutes or more. In yet another operational mode, the fan 144 may cycle between rotating and not rotating (e.g., off) for a duration of time, such as a few seconds or more, or a few minutes or more. A user may alternate between any of the foregoing operational modes by pressing and/or holding a first pushbutton 118 one or more times.

Figure 5:
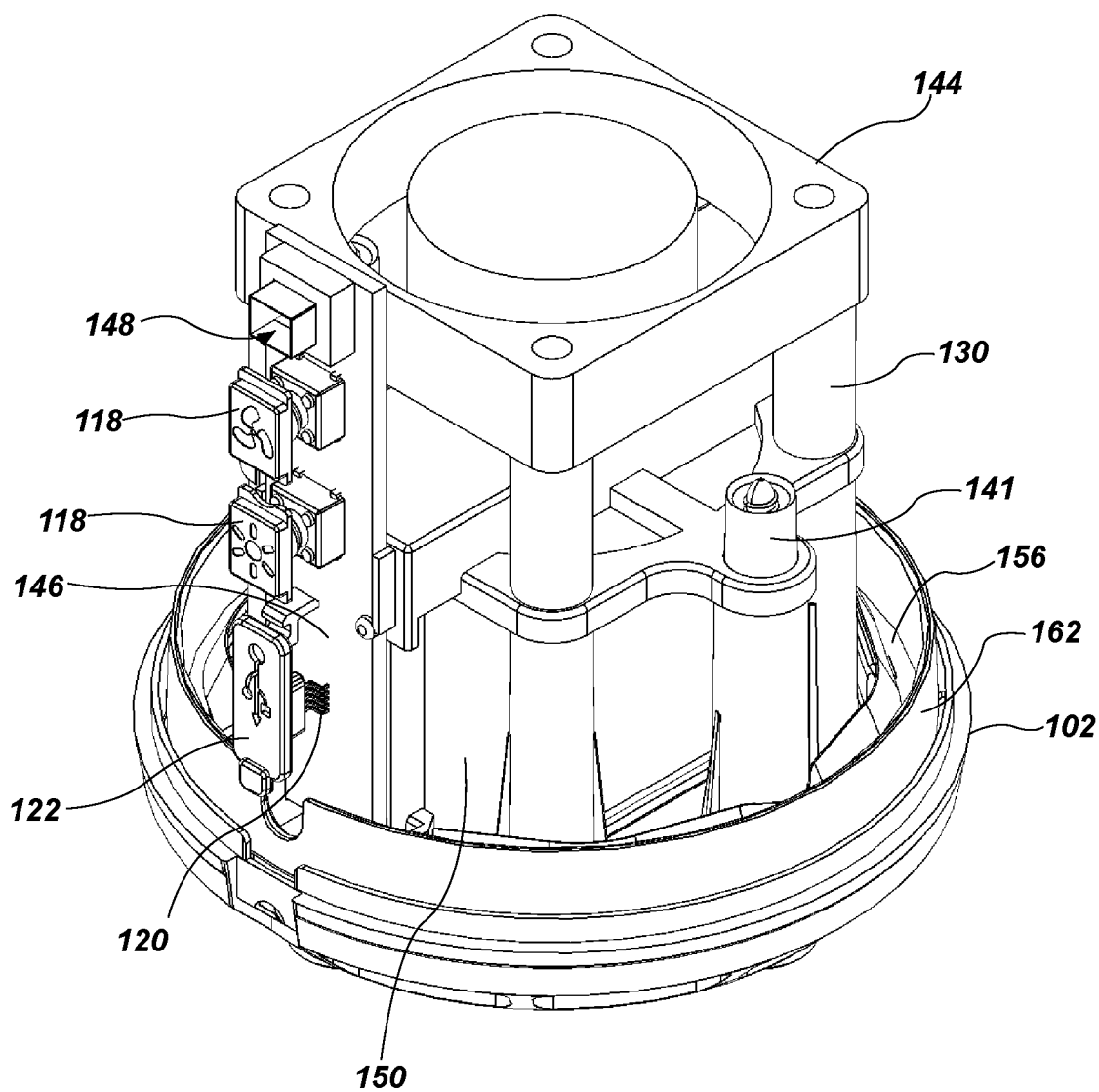
FIG. 5 is a perspective view of an internal portion of the diffuser of FIG. 1.

The fan 144 along with other elements located within (e.g., enclosed by) the sleeve 104 and/or located below the receptacle 136 are shown separately from the sleeve 104, the lid 106, the receptacle 136, and the plates 112, 124 in FIG. 5. With reference to FIG. 5, the diffuser 100 may further comprise a printed circuit board 146. The printed circuit board 146 may be mounted to the upper surface 103 of the base 102 and may extend vertically therefrom. The printed circuit board 146 may comprise a light emitting diode (LED) 148, one or more pushbuttons 118, and the USB connector 120 mounted thereon and electrically coupled thereto. The LED 148 may be visible through the opening 116 in the first plate 112. The LED 148 may be an indicator of an operational mode of the fan 144 and/or the lighting system of the diffuser 100 described in further detail below. The LED 148 may be configured to emit one or more colors of light. The LED 148 may be capable of emitting two or more colors of light, such as a white light and a green light.

The diffuser 100 may comprise a battery 150 mounted on the upper surface 103 of the base 102. The battery 150 may be located radially inward relative to the printed circuit board 146. In some embodiments, the battery 150 may comprise a lithium polymer battery. The battery 150 may be rechargeable by connecting the battery 150 to a power source. For example, the battery 150 may be connected to a power source via the USB connector 120 mounted on the printed circuit board 146. The diffuser 100 may be operable when connected to an external power supply. The diffuser 100 may also be operable by power supplied by the battery 150. In such embodiments, the diffuser 100 may be portable and usable in locations where an external power supply may be unavailable.

Figure 6:
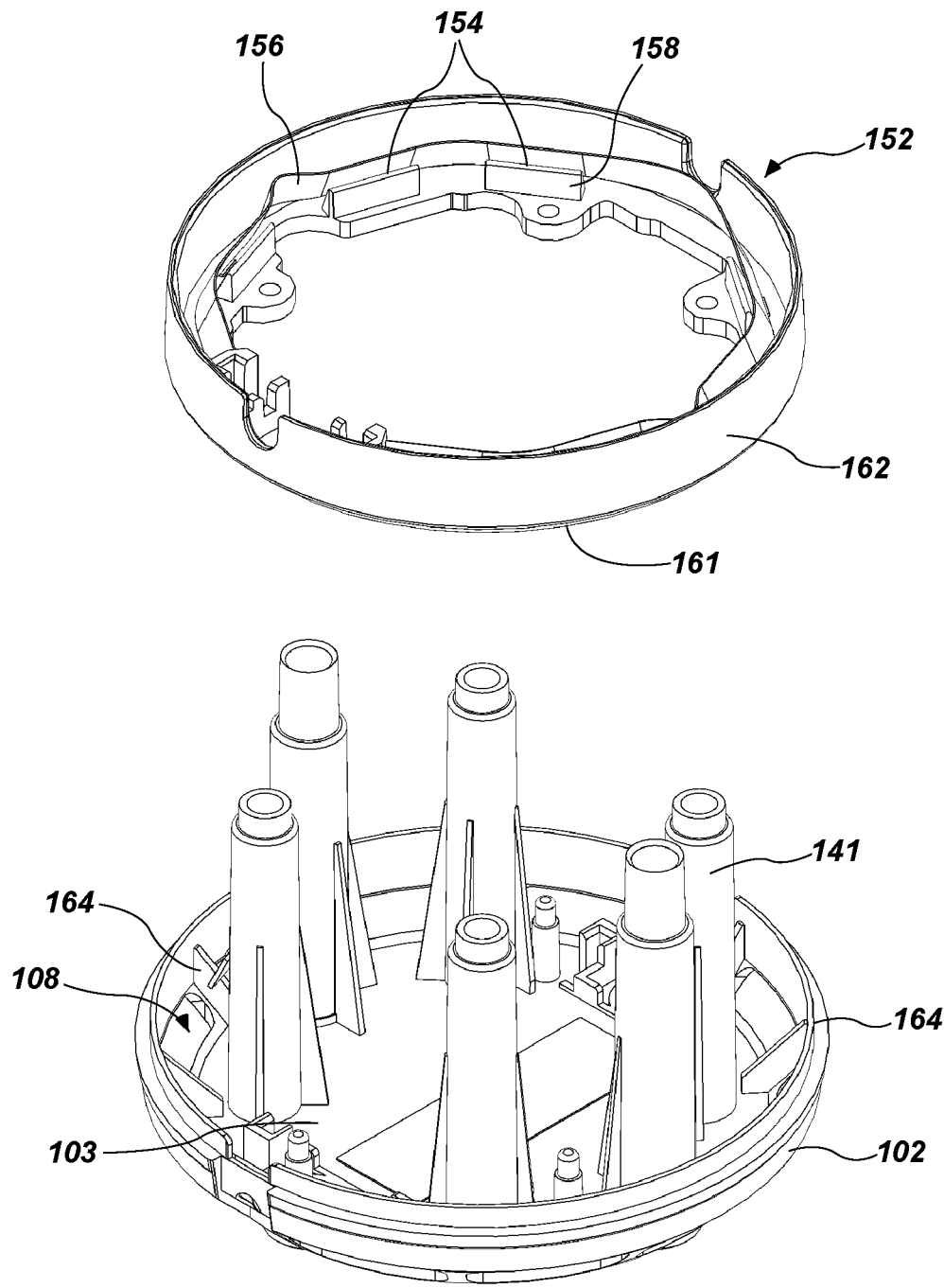
FIG. 6 is a perspective and exploded view of a base of the diffuser of FIG. 1.

The diffuser 100 may further comprise a lighting system. The lighting system is best illustrated in FIG. 6. FIG. 6 is an exploded view of the base 102 and an annular platform 152 having one or more LEDs 154 of the lighting system mounted thereon. The LEDs 154 may be mounted on support structures 158 provided on an upper surface 160 of the platform 152. A filter 156 configured to distribute light and eliminate hot spots of focused light generated by the LEDs 154 may be provided on the platform 152. The filter 156 may comprise an annular band of a substantially transparent or substantially translucent material. The filter 156 may be mounted between the LEDs 154 mounted on the support structures 158 and the sleeve 104 and, more particularly, between the LEDs 154 and a substantially vertically extending sidewall 162 of the platform 152. The platform 152 may be received within the base 102. More particularly, a lower surface 161 of the platform 152 may abut against and be supported by one or more posts 164. The posts 164 may be spaced about the periphery of the base 102 and may be provided between adjacent openings 108 such that the openings 108 are unobstructed by the posts 164. By supporting the platform 152 on the posts 164, air flow into the diffuser 100 through the openings 108 may be unrestricted by the lighting system.

The LEDs 154 may be electrically coupled to the printed circuit board 146. In operation, the LEDs 154 may generate light that may be visible from the exterior of the diffuser 100. The LEDs 154 may be spaced about the annular platform 152 adjacent to a perimeter of the platform 152 to evenly distribute light about a perimeter of the diffuser 100.

In some embodiments, at least one of the base 102, the sleeve 104, and the lid 106 may be at least substantially transparent or at least substantially translucent to light emitted by LEDs 154 (FIG. 6), such that light emitted by the LEDs 154 can pass therethrough. In other embodiments, at least one of the base 102, the sleeve 104, the lid 106, the first plate 112, and the second plate 124 may be opaque such that light emitted by the LEDs 154 cannot pass therethrough.

The LEDs 154 may be provided proximate to the base 102 such that light emitted by the LEDs 154 dissipates (e.g., reduces in intensity) along the sleeve 104 between the base 102 and the lid 106 creating an ombré effect. In some embodiments, the LEDs 154 may be capable of emitting two or more colors of light. For example, a user may be able to select whether the light emitted by the LEDs 154 is white, yellow, green, cyan, blue, magenta, or red. In one operational mode, the LEDs 154 may emit a single selected color. In another operational mode, the LEDs 154 may cycle through the various colors of light emitting each color for a duration of time, such as a few seconds or more, or a few minutes or more. In yet another operational mode, the LEDs 154 may emit more than one selected color. The operational modes of the LEDs may be selected by a user by pressing and/or holding a second pushbutton 118 one or more times.

With reference to any of FIGS. 3, 4, and 5, each of the fan 144, the printed circuit board 146, and the battery 150 may be located inward relative to the lighting system and, more particularly, relative to the LEDs 154 such that the fan 144, the printed circuit board 146, and the battery 150 do not cast shadows visible through the diffuser 100. In some embodiments, the plates 112, 124 may be opaque to prevent shadows of the LED 148, the pushbuttons 118, and the USB connector 120 from being visible through the diffuser 100.

Figure 7A:
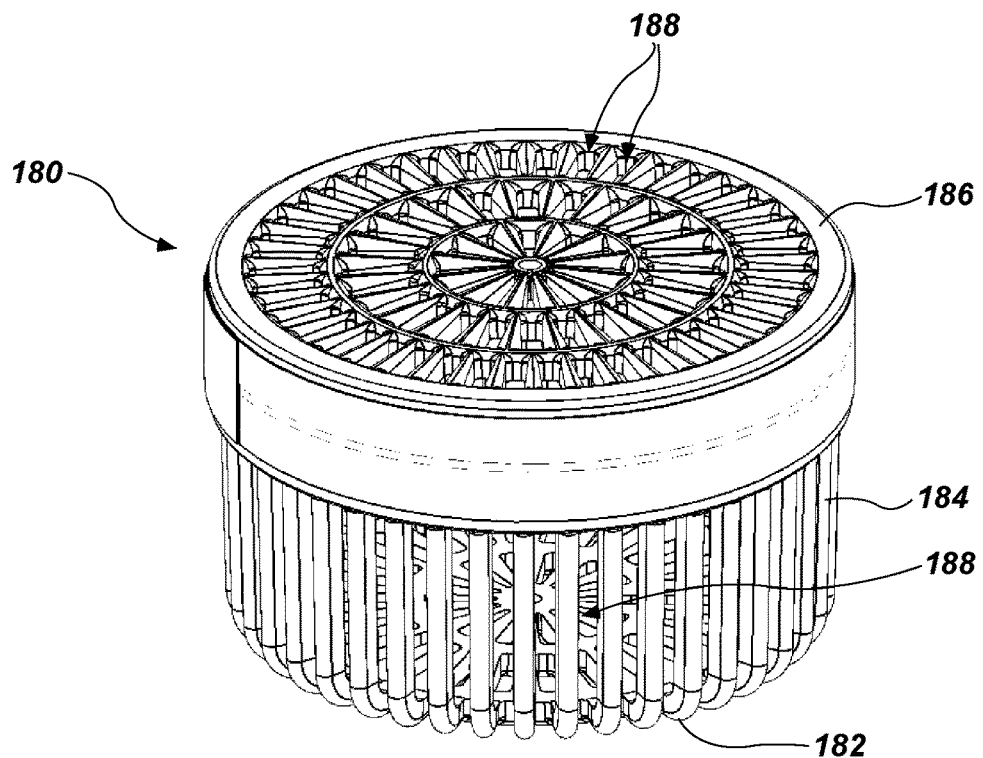
FIGS. 7A and 7B are perspective views of a container for retaining a fragrant medium therein.
Figure 7B:
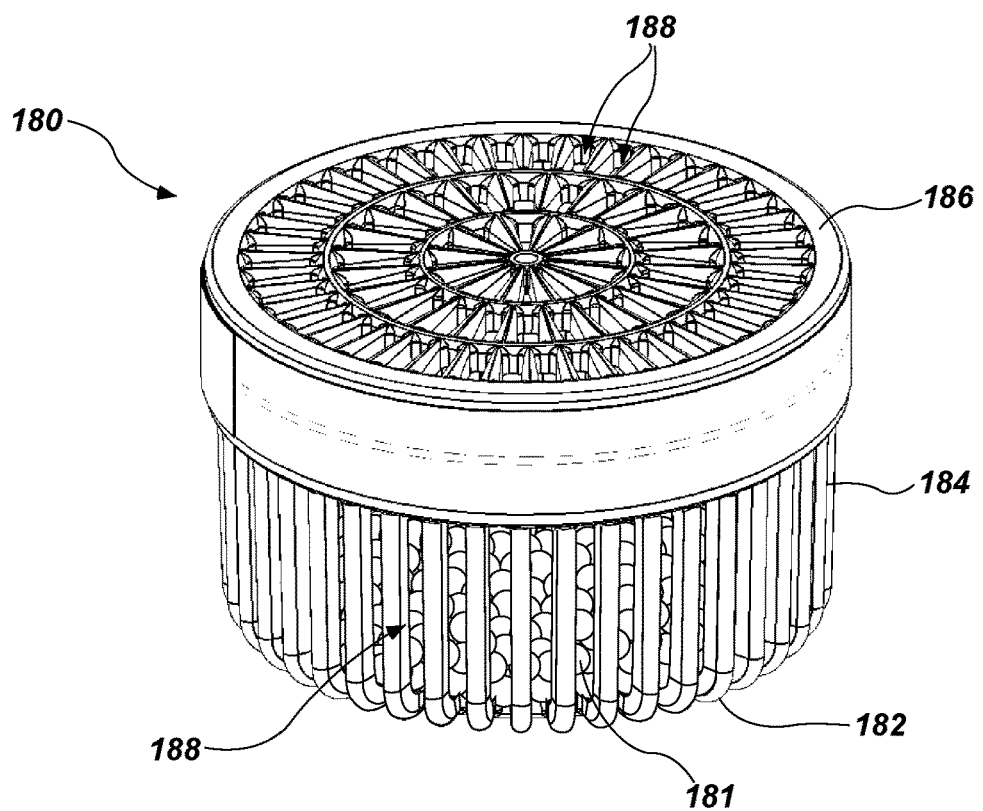
Figure 8:
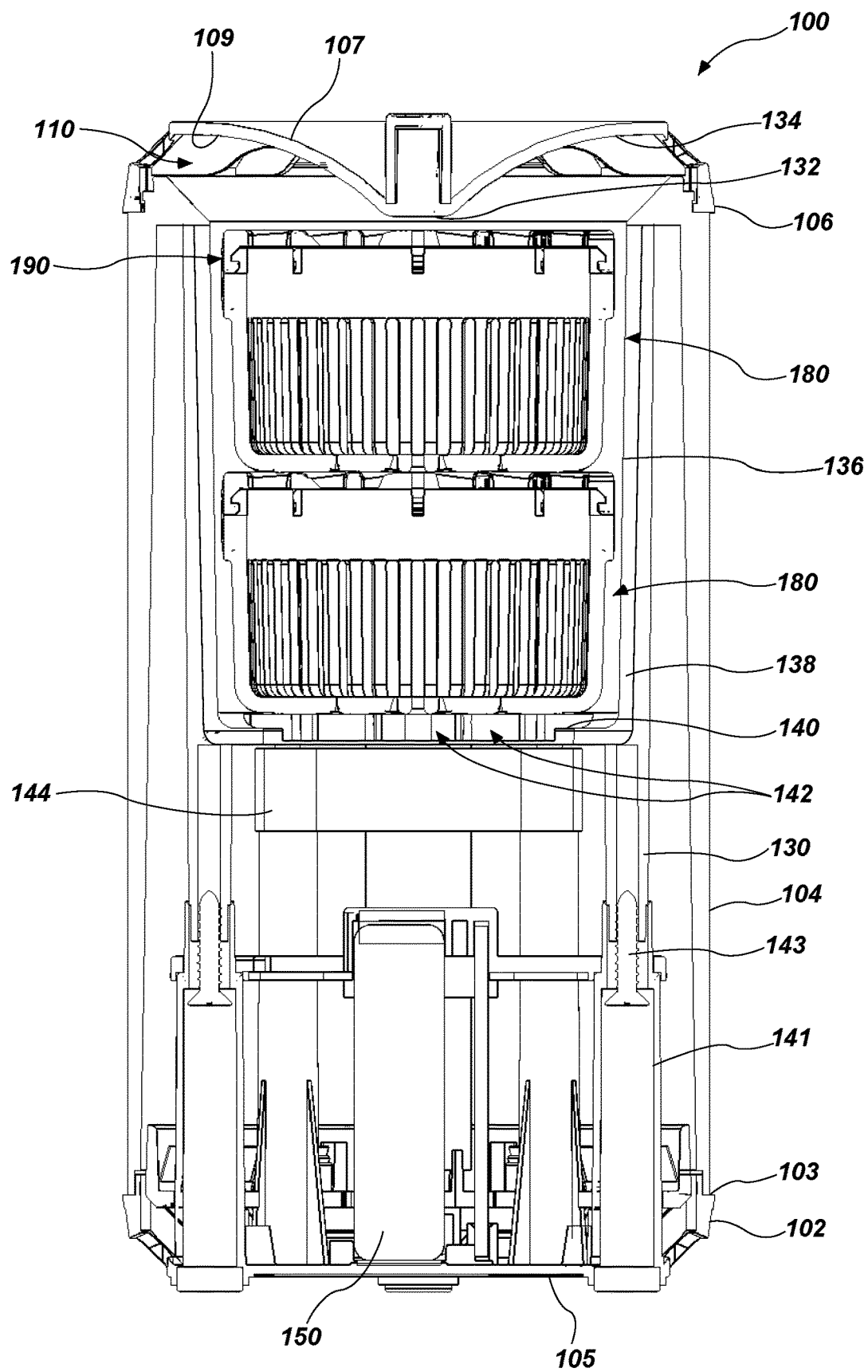
FIG. 8 is a cross-sectional view of the diffuser of FIG. 1 having the container of FIGS. 7A and 7B provided therein.

FIGS. 7A and 7B illustrate a perspective view of a container 180 that is empty in FIG. 7A and substantially filled with a fragrant medium 181 in FIG. 7B. As previously discussed, the receptacle 136 is configured to hold the fragrant medium 181 as illustrated in FIG. 7B. More particularly, in some embodiments, the fragrant medium 181 may also be retained within the container 180. Thus, the receptacle 136 may be sized and configured to retain one or more containers 180 as illustrated in FIG. 8. The fragrant medium 181 may comprise an at least partially solid fragrant medium. For example, the fragrant medium 181 may comprise a plastic casing filled (e.g., infused) with a fragrant liquid. The casing may be at least partially permeable to the fragrance (e.g., perfume) of the fragrant liquid enclosed therein such that the fragrant medium 181 emits a fragrance or scent detectable by a user.

The container 180 may comprise a bottom wall 182, a cylindrical and vertically extending sidewall 184, and a lid 186. In some embodiments, the lid 186 may be removably coupled to the sidewall 184 by threading 190 (FIG. 8) provided on the sidewall 184 and the lid 186. As best illustrated in FIG. 7A, each of the bottom wall 182, the sidewall 184, and the lid 186 may comprise a plurality of openings 188 formed therein. In some embodiments, the openings 188 may be oblong such that a first dimension is greater than second dimension and, more particularly, such that a first dimension measured in a first direction is greater than a second dimension measured in a second direction substantially transverse to the first direction. In some embodiments, the openings 188 in the bottom wall 182 and the lid 186 may have a greater length (e.g., radially extending dimension) and a lesser width, and the openings 188 in the sidewalls 184 may have a greater height (e.g., vertically extending dimension) and a lesser width (e.g., circumferentially extending dimension). In other embodiments, the openings 188 in the bottom walls 182 and the lid 186 may have a lesser length and a greater width, and/or the openings 188 in the sidewalls 184 may have a lesser height and a greater width. In yet other embodiments, the openings 188 in one or more of the bottom wall 182, sidewall 184, and lid 186 may comprise equal transverse dimensions. In any of the foregoing embodiments, the openings 188 may have at least one dimension that is less than a smallest dimension of the fragrant medium 181 such that the fragrant medium 181 is not removable through the openings 188. In some embodiments, the fragrant medium 181 may be at least one of spherical, cylindrical, and lenticular in shape. A smallest dimension of the fragrant medium 181, such as a diameter of the fragrant medium, may be greater than or equal to about 2.0 mm. In other embodiments, the smallest dimension of the fragrant medium 181 may extend in a range from about 2.0 mm to about 10.0 mm, from about 2.0 mm to about 7.0 mm, and from about 2.0 mm to about 5.0 mm. In such embodiments, the openings 188 may have at least one dimension that is less than about 2.0 mm, such as about 1.6 mm.

The receptacle 136 may be sized to receive at least one container 180 therein. As illustrated in the cross-sectional view of the diffuser 100 in FIG. 8, the diffuser 100 may receive two containers 180. In some embodiments, the fragrant medium 181 provided in the respective containers 180 may comprise a different scent or perfume such that a user can vary and mix the fragrance emitted by the diffuser 100. The containers 180 may be stackable without obstructing the openings 188 in the bottom wall 182 and lid 186.

Embodiments of the present disclosure further include methods of assembly the diffuser 100. The diffuser 100 may be part of a kit that may not include the containers 180 having the fragrant medium 181 retained therein. The containers 180 may be interchangeable within the diffuser 100 so as to allow a user to alter the fragrance emitted in the forced airflow by the diffuser 100. Therefore, a method of assembling the diffuser 100 may include providing the diffuser 100, removing the lid 106 from the sleeve 104 by disengaging the threading 128 provided therebetween, and disposing at least one container 180 retaining the fragrant medium 181 in the receptacle 136. As illustrated in FIG. 8, the receptacle 136 may be sized and configured to receive two containers 180 therein. The lid 106 may be coupled to the sleeve 104 prior to operation of the diffuser 100.

Embodiments of the present disclosure further include methods of using the diffuser 100. Such methods include providing the diffuser 100, removing the lid 106 from the sleeve 104 by disengaging the threading 128 provided therebetween, disposing at least one container 180 retaining the fragrant medium 181 in the receptacle 136, and coupling the lid 106 to the sleeve 104. Subsequently, power may be supplied to the diffuser 100 via power stored in the battery 150 and/or by coupling the battery 150 to an external power source via the USB connector 120 and a USB connector cable. More particularly, power may be supplied to the fan such that airflow is forced from an exterior of the diffuser 100, into the base 102 through the openings 108, through the openings 142 in the bottom wall 140 of the receptacle 136, through the containers 180 and about the fragrant medium 181 disposed in the receptacle 136, to a volume of space above the receptacle 136 and enclosed by the lid 106, and through the openings 116 in the lid 106 to ambient air external to the diffuser 100 such that the fragrance emitted by the fragrant medium 181 is carried by the forced airflow to the ambient air external to the diffuser 100. As previously described, the method may also include altering the operational mode of the fan by pressing and/or holding the pushbutton 118. Power may also be supplied to the LEDs 154 and LED 148. As previously described, the method may also include alternating the operational mode of the LEDs 154 by pressing and/or holding the other pushbutton 118.

While the present invention has been described herein with respect to certain embodiments, those of ordinary skill in the art will recognize and appreciate that it is not so limited. Rather, many additions, deletions, and modifications to the embodiments depicted and described herein may be made without departing from the scope of the invention as hereinafter claimed, and legal equivalents. In addition, features from one embodiment may be combined with features of another embodiment while still being encompassed within the scope of the invention as contemplated by the inventor. Further, the invention has utility in diffusers having different designs and configurations than those shown and described herein.

What is claimed is:

1. A diffuser for diffusing a fragrant air into surrounding ambient air, comprising:
    a base comprising at least one opening, the at least one opening formed about a periphery of the base and extending between a lower surface and an upper surface of the base;
    a fan mounted to the base over the upper surface thereof;
    a receptacle provided over the fan and mounted to the base over the upper surface thereof, the receptacle comprising a bottom wall and a vertically extending sidewall to retain a fragrant medium therein, the bottom wall comprising a plurality of openings formed therethrough;
    a sleeve mounted on the upper surface of the base and enclosing the fan and the receptacle; and
    a lid mounted over the sleeve, the lid comprising at least one opening, the at least one opening formed about a periphery of the lid and extending between a lower surface and an upper surface of the lid, wherein the lower surface of the lid has a frustoconical shape, the frustoconical shape comprising a planar central surface and a curved sidewall extending circumferentially about the planar central surface and radially outward toward the periphery of the lid;
    wherein the fan is configured to force airflow from an exterior of the diffuser, into the base through the at least one opening of the base, through the plurality of openings formed in the bottom wall of the receptacle, through the receptacle and about any fragrant medium therein, into a volume of space above the receptacle and enclosed by the lid, and out through the at least one opening in the lid to the ambient air external to the diffuser.

2. The diffuser of claim 1, wherein the sleeve is integrally formed with the receptacle.

3. The diffuser of claim 1, wherein an exterior surface of at least one of the base, the sleeve, and the lid is textured.

4. The diffuser of claim 1, wherein the fragrant medium is at least partially solid.

5. The diffuser of claim 1, wherein the fragrant medium comprises a fragrant fluid enclosed in a plastic casing.

6. The diffuser of claim 1, further comprising a container provided in the receptacle, the container retains the fragrant medium therein.

7. The diffuser of claim 6, wherein:
the container comprises a bottom wall, a sidewall, and a lid; and
each of the bottom wall, the sidewall, and the lid comprises a plurality of openings formed therethrough.

8. The diffuser of claim 7, wherein at least one dimension of the plurality of openings has a measure less than a smallest dimension of the fragrant medium such that the fragrant medium is not removable through the plurality of openings.

9. The diffuser of claim 1, further comprising at least one light-emitting diode (LED) mounted on an upper surface of a platform, the platform supported on at least one support structure extending from the upper surface of the base.

10. The diffuser of claim 9, wherein the light emitted by the at least one LED is visible from the exterior of the diffuser.

11. The diffuser of claim 9, further comprising a filter configured to distribute light and eliminate spots of focused light generated by the at least one LED, the filter mounted on the upper surface of the platform and between the at least one LED and the sleeve.

12. A method of assembling a diffuser for diffusing fragrant air into surrounding ambient air, comprising:
providing a diffuser, comprising:
a base comprising at least one opening, the at least one opening formed about a periphery of the base and extending between a lower surface and an upper surface of the base;
a fan mounted to the base over the upper surface thereof;
a receptacle provided over the fan and mounted to the base over the upper surface thereof, the receptacle comprising a bottom wall and a vertically extending sidewall, the bottom wall comprising a plurality of openings formed therethrough; and
a sleeve mounted on the upper surface of the base and enclosing the fan and the receptacle;
disposing an at least partially solid fragrant medium in the receptacle; and
coupling a lid to the sleeve, the lid comprising at least one opening formed about a periphery of the lid and extending between a lower surface and an upper surface of the lid, wherein the lower surface of the lid has a frustoconical shape, the frustoconical shape comprising a planar central surface and a curved sidewall extending circumferentially about the planar central surface and radially outward toward the periphery of the lid, and wherein the fan is configured to force airflow from an exterior of the diffuser, into the base through the at least one opening of the base, through the plurality of openings formed in the bottom wall of the receptacle, through the receptacle and about the at least partially solid fragrant medium therein, into a volume of space above the receptacle and enclosed by the lid, and out through the at least one opening in the lid to the ambient air external to the diffuser.

13. The method of claim 12, wherein the step of disposing the at least partially solid fragrant medium in the receptacle comprises disposing a container having a bottom wall, a sidewall, and a lid within the receptacle, the container having the at least partially solid fragrant medium disposed therein.

14. The method of claim 13, further comprising selecting each of the bottom wall, the sidewall, and the lid of the container to comprise at least one opening extending therethrough.

15. The method of claim 14, further comprising selecting the at least one opening of each of the bottom wall, the sidewall, and the lid to have at least one dimension less than or equal to 1.6 mm.

16. A method of using a diffuser for diffusing a fragrance into surrounding ambient air, comprising:
providing a diffuser, comprising:
a base comprising at least one opening, the at least one opening formed about a periphery of the base and extending between a lower surface and an upper surface of the base;
a fan mounted to the base over the upper surface thereof;
a receptacle provided over the fan and mounted to the base over the upper surface thereof, the receptacle comprising a bottom wall and a vertically extending sidewall, the bottom wall comprising a plurality of openings formed therethrough; and
a sleeve mounted on the upper surface of the base and enclosing the fan and the receptacle;
disposing an at least partially solid fragrant medium within the receptacle, the at least partially solid fragrant medium emitting a fragrance;
providing a lid on the sleeve, the lid having at least one opening formed about a periphery thereof, the at least one opening extending between a lower surface and an upper surface of the lid, wherein the lower surface of the lid has a frustoconical shape, the frustoconical shape comprising a planar central surface and a curved sidewall extending circumferentially about the planar central surface and radially outward toward the periphery of the lid; and
supplying power to the fan such that airflow is forced from an exterior of the diffuser, into the base through the at least one opening of the base, through the plurality of openings formed in the bottom wall of the receptacle, through the receptacle and about the at least partially solid fragrant medium therein, into a volume of space above the receptacle and enclosed by the lid, and out through the at least one opening in the lid to ambient air external to the diffuser and such that the fragrance emitted by the at least partially solid fragrant medium is carried by the airflow to the ambient air external to the diffuser.

17. The method of claim 16, wherein the step of supplying power to the fan comprises providing power from a battery to the fan, the battery mounted over the upper surface of the base.

18. The method of claim 16, wherein the step of disposing the at least partially solid fragrant medium within the receptacle comprises providing a container having the at least partially solid fragrant medium disposed therein within the receptacle.

19. The method of claim 18, further comprising providing two containers each having the at least partially solid fragrant medium disposed therein within the receptacle.

* * * * *